United States Patent [19]
Yoo

[11] Patent Number: 5,665,900
[45] Date of Patent: Sep. 9, 1997

[54] APPARATUS FOR TESTING WEAR-RESISTANCE OF A PINCH ROLLER TO BE INCORPORATED IN A VIDEO CASSETTE RECORDER

[75] Inventor: Dae-Sun Yoo, Seoul, Rep. of Korea

[73] Assignee: Daewoo Electronics Co., Ltd., Seoul, Rep. of Korea

[21] Appl. No.: 639,414

[22] Filed: Apr. 29, 1996

[30] Foreign Application Priority Data

Apr. 29, 1995 [KR] Rep. of Korea ............... 95-9189

[51] Int. Cl.⁶ .................................................. G01N 3/56
[52] U.S. Cl. ................................................................ 73/7
[58] Field of Search ................................... 73/7, 865.9

[56] References Cited

U.S. PATENT DOCUMENTS

| | | | |
|---|---|---|---|
| 3,753,093 | 8/1973 | Gardner et al. ................ | 73/7 X |
| 4,235,091 | 11/1980 | Takano et al. ................ | 73/7 |
| 4,372,172 | 2/1983 | Gombolz et al. ............ | 73/7 X |
| 4,459,842 | 7/1984 | Kihara et al. ................ | 73/7 |
| 5,533,382 | 7/1996 | Clerkin ........................ | 73/7 |

*Primary Examiner*—Thomas P. Noland
*Attorney, Agent, or Firm*—Pennie & Edmonds LLP

[57] ABSTRACT

An apparatus for testing wear-resistance of a pinch roller comprises a base provided with at least one post; a drum rotatably mounted on the base, wherein a tape is wound around an circumferential surface thereof; a driving motor; a tape holding member and a blind hole which is formed on the drum, the tape holding member being tightly inserted into the blind hole while the tape is tightened to hold the tape tightened; and a pinch roller holder pivotally mounted on the base, wherein a pinch roller to be tested is rotatably mounted on one end portion thereof and the other end portion is selectively connected to the post through an elastic member, thereby allow the pinch roller to resiliently press the tape against the drum.

5 Claims, 6 Drawing Sheets

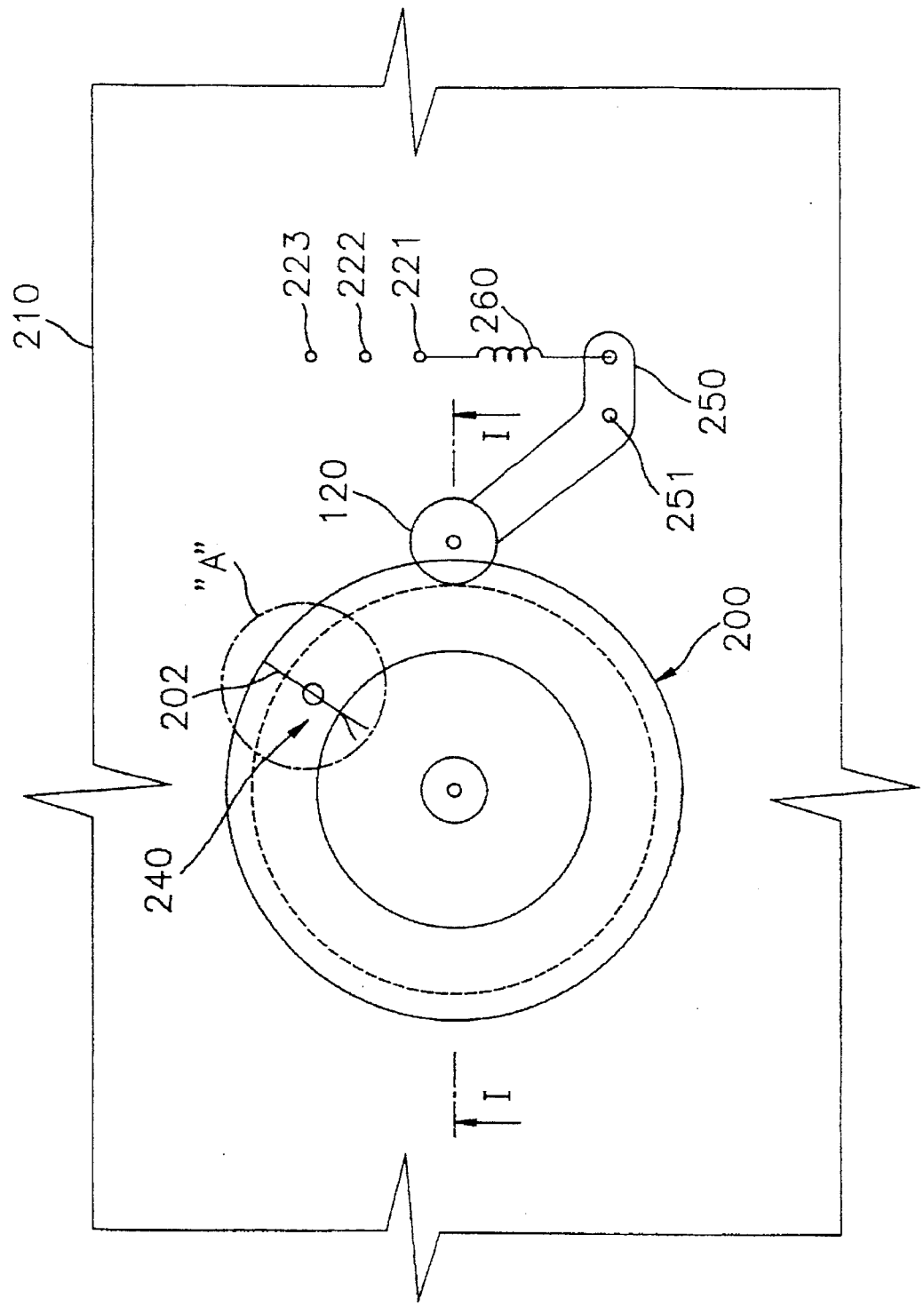

APPARATUS FOR TESTING WEAR-RESISTANCE OF A PINCH ROLLER TO BE INCORPORATED IN A VIDEO CASSETTE RECORDER

FIELD OF THE INVENTION

The present invention relates to a video cassette recorder ("VCR"); and, more particularly, to an apparatus for testing wear-resistance of a pinch roller to be incorporated therein, the apparatus being simple and capable of providing a reliable result in a much shortened period of time.

DESCRIPTION OF THE PRIOR ART

There is shown in FIG. 1 a schematic top view of a conventional apparatus for testing wear-resistance of a pinch roller to be incorporated in a VCR. The test apparatus normally includes a pair of reel tables 1, 2, a head drum 60, a pair of pole base 40, a full-erasing head 30, an audio control head assembly 90, a capstan shaft 110, a capstan motor(not shown) and a pinch roller 120. In a wear-resistance test of the pinch roller 120, the pinch roller 120 presses a magnetic tape T against the capstan shaft 110 which is rotated by the capstan motor, with the tape T travelling therebetween.

However, in such a conventional apparatus, due to a small diameter of the capstan shaft 110, the contact surface area between the pinch roller 120 and the capstan shaft 110 per one revolution of the capstan shaft 110 is relatively small. In other words, in order to obtain an experimentally reliable test result, the wear-resistance test must be performed over an extended period of time, e.g., more than 1,000 hours. In addition, since the apparatus includes a number of components, other than the pinch roller and the capstan shaft, which may influence the test result, the wear-resistance of the pinch roller 120 cannot be measured accurately.

SUMMARY OF THE INVENTION

It is, therefore, a primary object of the invention to provide an apparatus for testing wear-resistance of a pinch roller to be incorporated in a VCR, which is simple and is capable of providing an experimentally reliable result in a much shortened period of time.

In accordance with one aspect of the present invention, there is provided an apparatus for testing wear-resistance of a pinch roller, comprising: a base provided with at least one post; a drum rotatably mounted on the base, wherein a tape is wound around a circumferential surface thereof; means for rotating the drum; means for holding the tape; and a pinch roller holder pivotally mounted on the base, wherein the pinch roller to be tested is rotatably mounted on one end portion thereof and the other end portion is selectively connected to the post through an elastic member, thereby allowing the pinch roller to resiliently press the tape against the drum.

BRIEF DESCRIPTION OF THE DRAWINGS

The above and other objects and features of the instant invention will become apparent from the following description of preferred embodiments taken in conjunction with the accompanying drawings, in which:

FIG. 2A illustrates a schematic top view of a preferred embodiment of an apparatus for testing the wear-resistance of the pinch roller in accordance with the present invention;

DETAILED DESCRIPTION OF THE PREFERRED EMBODIMENTS

Figure 1:
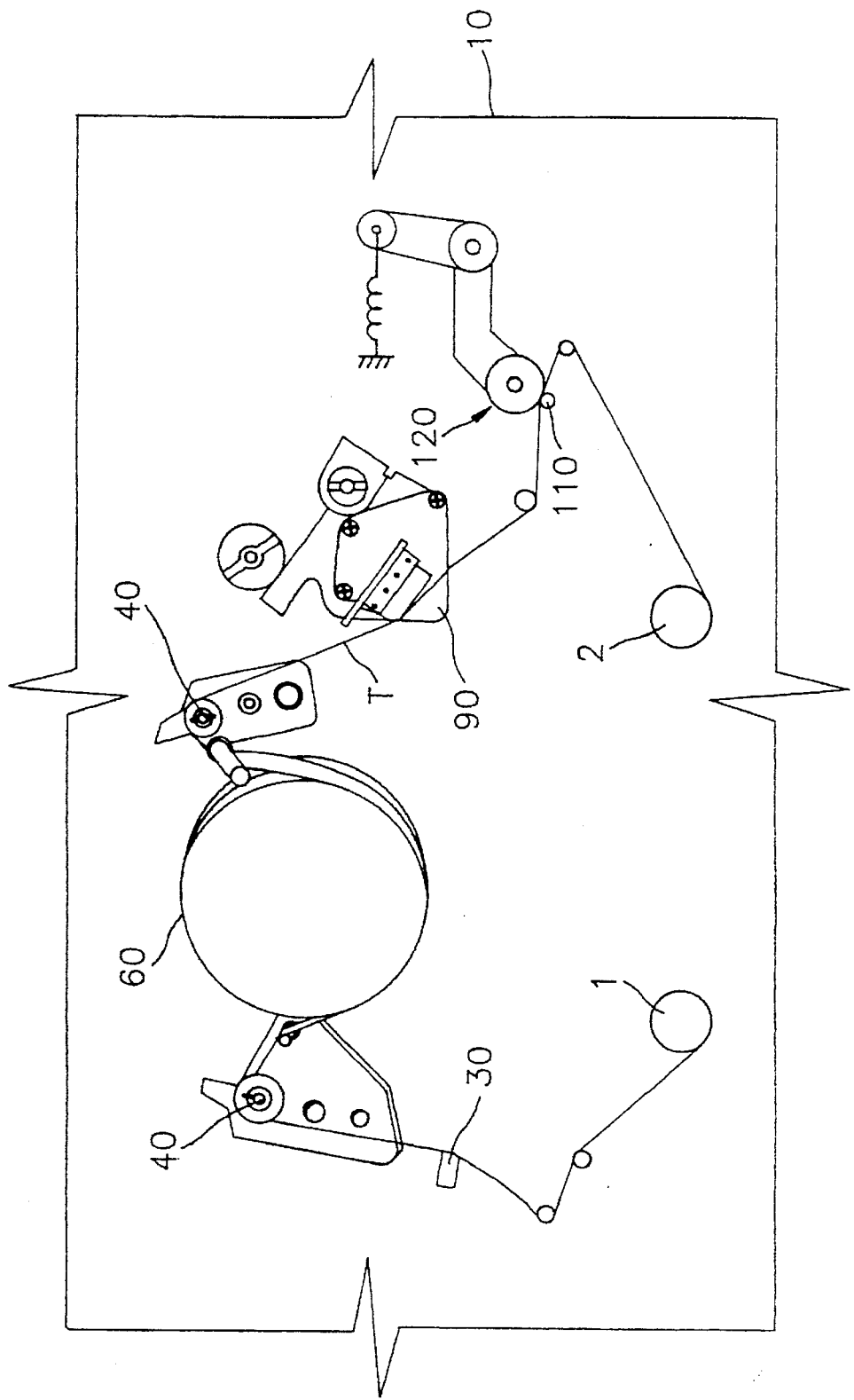
FIG. 1 represents a schematic top view of a conventional apparatus for testing wear-resistance of a pinch roller.

There are shown in FIGS. 2A to 2D various views of a preferred embodiment of an apparatus for testing wear-resistance of a pinch roller to be incorporated in a VCR in accordance with the present invention. The inventive test apparatus includes a base 210, a drum 200 provided with a pair of tape guide portions 230, a driving motor 300, a pinch roller holder 250, a tape holding means 240 and a post 221.

Figure 2B:
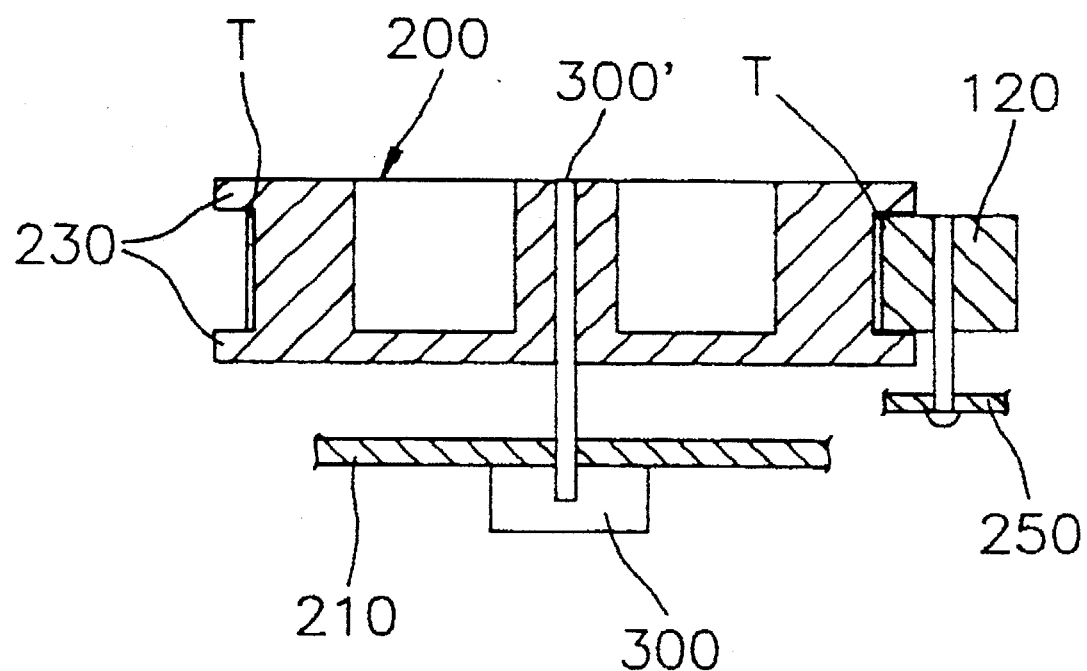
FIG. 2B sets forth a cross-sectional view taken along line I—I of FIG. 2A.

Referring to FIGS. 2A and 2B, the driving motor 300 is fixed on the base 210 in such away that a rotating shaft 300' thereof is rotatable. The drum 200 having a split 202 is mounted to the rotating shaft 300' and rotates therewith. The tape guide portions 230 for guiding a magnetic tape T are formed on an upper and a lower portions of a circumferential surface of the drum 200 and protrude radially outwardly therefrom, respectively, preventing the tape T from deviating from the drum 200.

Figure 2C:
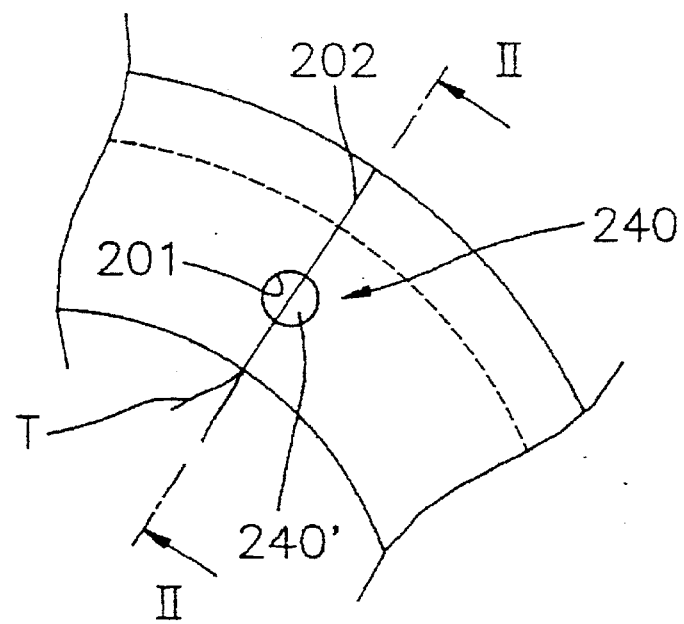
FIG. 2C presents an enlarged view of the portion "A" of FIG. 2A.
Figure 2D:
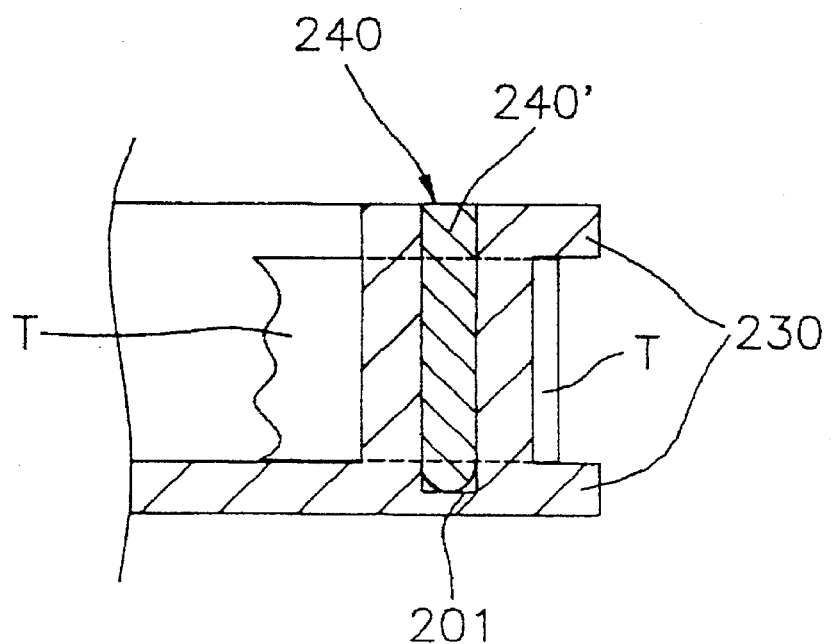
FIG. 2D demonstrates a cross-sectional view taken along line II—II of FIG. 2C.

The tape holding means 240 includes a tape holding member 240' and a blind hole 201 which is formed on a top surface of the drum 200 in such a way that the split 202 goes through the blind hole 201 as shown in FIGS. 2C and 2D. The magnetic tape T, which has a greater length than the circumferential length of the drum 200, is wound around the circumferential surface of the drum 200 between the tape guide portions 230 and both ends thereof pass through the split 202 and the blind hole 201 into an inside of the drum 200. The tape holding member 240' is, then, tightly inserted into the blind hole 201 while the tape T is held tightly, thereby tightening the hold of the tape T.

On the other hand, referring back to FIG. 2A, the pinch roller holder 250 is pivotally mounted on the base 210 through a hinge pin 251. The pinch roller 120 to be tested is rotatably mounted on one end portion of the pinch roller holder 250. The other end portion of the pinch roller holder 250 is connected to the post 220 through a spring 260. At test of the wear-resistance of the pinch roller 120, the tensile force of the spring 260 allows the pinch roller 120 to resiliently press the tape T against the drum 200 while the drum 200 is rotated by the driving motor 300.

Preferably, there are mounted on the base 220 a plurality of, e.g., three posts 221, 222 and 223, located at different distances from the pinch roller holder 250 to allow an easy adjusting of the tensile force of the spring 260 and hence the pressing force of the pinch roller 120 (In practice, the pressing force of the pinch roller 120 is 1.2 kgf). In addition, it is preferable that the drum be made of stainless steel, same as the capstan shaft incorporated in the VCR.

Figure 3A:
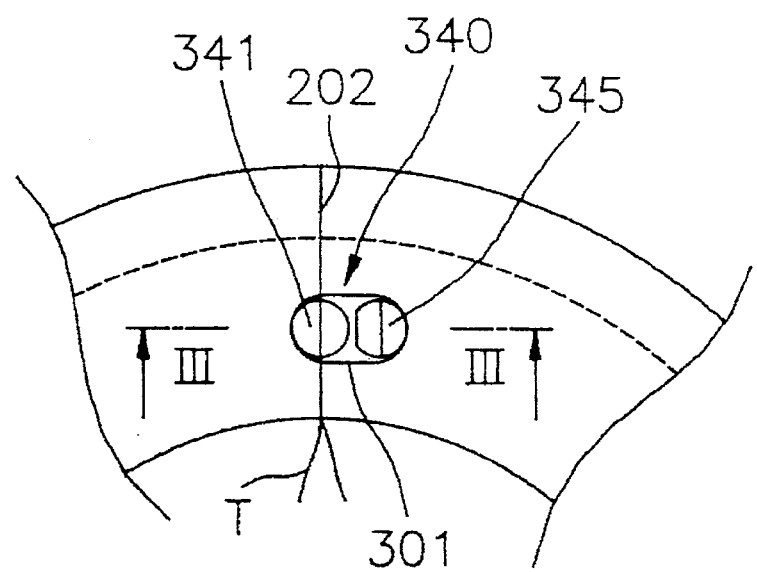
FIG. 3A depicts an enlarged view of the portion corresponding to the portion "A" of FIG. 2A for another preferred embodiment of the test apparatus.
Figure 3B:
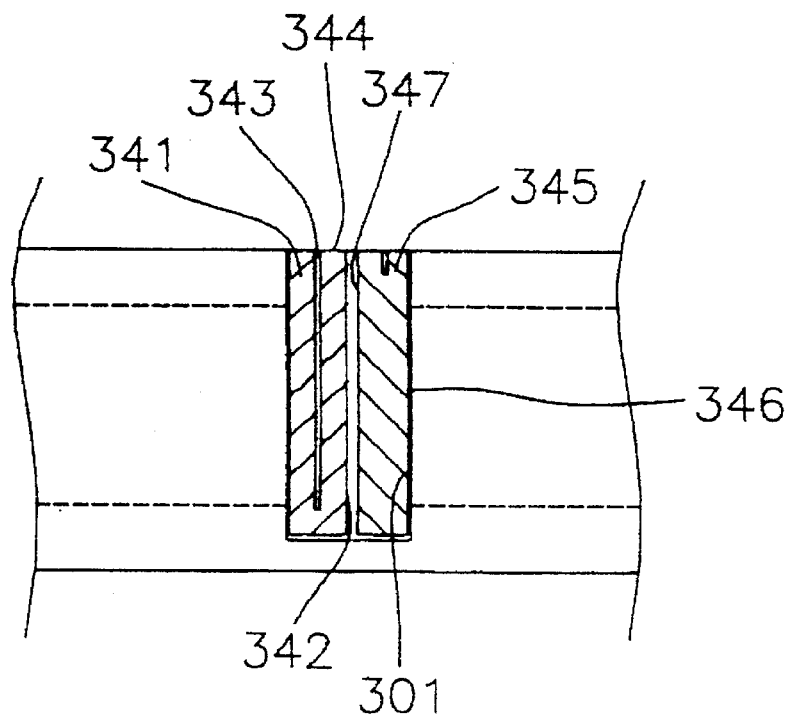
FIG. 3B is a cross-sectional view taken along line III—III of FIG. 3A.
Figure 4A:
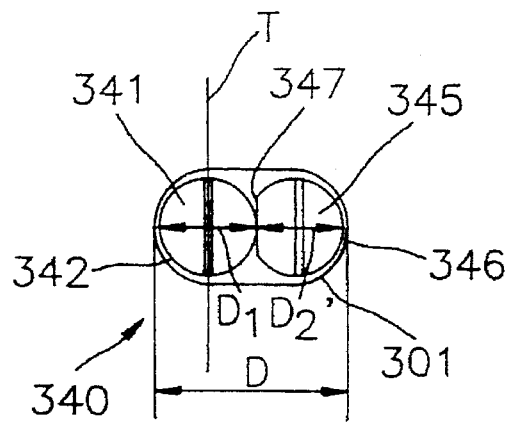
FIGS. 4A to 4C depict different stages in which the tape holding member and the locking member shown in FIGS. 3A and 3B, respectively, interact.

There is shown in FIGS. 3A and 3B another preferred embodiment of the present invention. The second preferred embodiment is similar to the first except for a tape holding means 340. The tape holding means 340 includes a cylindrical tightening member 341, a locking member 345 part of whose cylindrical side is cut to thereby make a flat side surface parallel to the central axis thereof, and a substantially ellipse-shaped blind hole 301 which is formed on the top surface of the drum 200 such that the split 202 goes through the ellipse-shaped blind hole 301, wherein the longitudinal length D of the ellipse-shaped blind hole 301 is slightly smaller than the sum of a diameter D1 of the tightening member 341 and a diameter D2 of the locking member 345 and is slightly larger than the sum of the diameter D1 of the tightening member 341 and a lenth D2' of the locking member 345, wherein the lenth D2' is the sum of a radius of the locking member 345 and a perpendicular distance between the flat side surface 347 and the central axis of the locking member 345, as seen in FIGS. 4A to The tightening member 341 is provided with an outer surface 342, a top surface 344 and a slit 343. The slit 343, which has a depth greater than the width of the tape, crosses the tightening member 341 along the central line thereof and extends from the top surface 344 longitudinally downwardly. The tightening member 341 and the locking member 345 are inserted into the blind hole 301 in such a way that the flat surface 347 of the locking member 345 faces the tightening member 341 and the slit 343 is located in line with the split 202 of the drum 200.

Figure 4B:
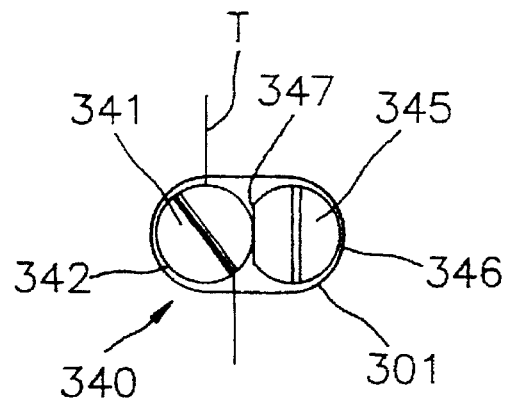
Figure 4C:
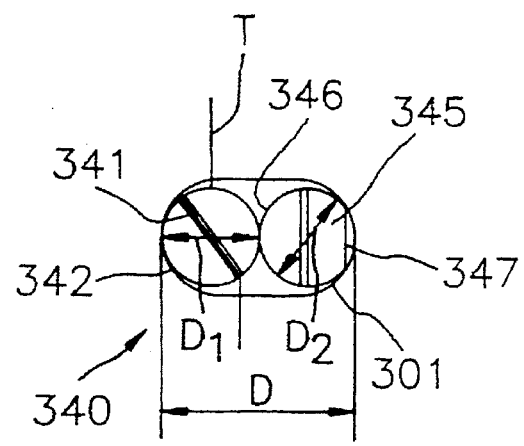

The manner in which the tightening member 341 and the locking member 345 interact will now be described using FIGS. 4A to 4C.

Both ends of the magnetic tape which is wound around the circumferential surface of the drum 200 pass through the split 202 of the drum 200 and the slit 343 of the tightening member 341. The tightening member 341 is rotated until the tape T becomes tightened and, then, the locking member 345 is rotated, e.g., counterclockwise, by using an appropriate tool, e.g., driver, till the cylindrical surface 346 of the locking member 345 faces the tightening member 341 so that the tightening member 341 is urged towards the surface of the blind hole 301, and the tightening member 341 and the locking member 345 are stuck in the substantially ellipse-shaped blind hole 301, thereby holding the tape tightly as shown in FIG. 4C.

In the inventive test apparatus of the present invention, since the contact surface area between the drum and the pinch roller per one revolution of the drum is much larger than in the prior art, the wear-resistance of pinch roller can be measured in a much shortened period of time. Furthermore, by removing the other components which may influence the result, an accurate test result can be obtained Although the invention has been shown and described with respect to the preferred embodiments, it will be understood by those skilled in the art that various changes and modifications may be made without departing from the spirit and scope of the invention as defined in the following claims.

What is claimed is:

1. An apparatus for testing wear-resistance of a pinch roller, comprising:

a base provided with at least one post;

a drum rotatably mounted on the base, wherein a tape is wound around an circumferential surface thereof;

means for rotating the drum;

means for holding the tape; and a pinch roller holder pivotally mounted on the base, wherein a pinch roller to be tested is rotatably mounted on one end portion thereof and the other end portion is. selectively connected to the post through an elastic member, thereby allowing the pinch roller to resiliently press the tape against the drum.

2. The apparatus of claim 1, wherein the drum is provided with a split, ends of the tape passing therethrough into an inside of the drum.

3. The apparatus of claim 2, wherein the tape holding means is provided with a tape holding member and a blind hole which is formed on the drum such that the split goes therethrough and the both ends of the tape pass through the split and the blind hole into an inside of the drum, and the tape holding member being tightly inserted into the blind hole while the tape is held tightly, thereby holding the tape tightly.

4. The apparatus of claim 2, wherein the tape holding means includes a substantially ellipse-shaped blind hole which is formed on the drum such that the split goes therethrough, a cylindrical tightening member and a locking member part of whose cylindrical side is cut to thereby make a flat side surface parallel to the central axis thereof, the tightening member being provided with an outer surface, a top surface and a slit, the slit having a depth greater than the width of the tape, the tightening member and the locking member being inserted into the blind hole in such a way that the flat side surface of the locking member faces the tightening member and the slit is located in line with the split of the drum and the both ends of the tape pass through the split and the slit into an inside of the drum, the tightening member being rotated until the tape becomes tightened and, then, the locking member being rotated so that the tightening member and the locking member are stuck in the ellipse-shaped blind hole, thereby the tape being held tightly.

5. The apparatus of claim 1, wherein the drum is provided with tape guide portions, the tape guide portions formed on an upper and a lower portion of the circumferential surface thereof and protruding radially outwardly therefrom, respectively.

\* \* \* \* \*